US006331633B1

(12) United States Patent
Neogi et al.

(10) Patent No.: US 6,331,633 B1
(45) Date of Patent: Dec. 18, 2001

(54) HETEROCYCLIC ANALOGS OF DIPHENYLETHYLENE COMPOUNDS

(75) Inventors: Partha Neogi; Bishwajit Nag, both of Fremont; Satyanarayana Medicherla, Sunnyvale; Debendranath Dey, Union City, all of CA (US)

(73) Assignee: Calyx Therapeutics Inc., Hayward, CA (US)

( * ) Notice: Subject to any disclaimer, the term of this patent is extended or adjusted under 35 U.S.C. 154(b) by 0 days.

(21) Appl. No.: 09/287,237

(22) Filed: Apr. 6, 1999

Related U.S. Application Data

(63) Continuation-in-part of application No. 09/074,925, filed on May 8, 1998, now Pat. No. 6,245,814.

(51) Int. Cl.$^7$ ................................................. H61K 31/425
(52) U.S. Cl. ........................... 548/183; 548/227; 548/226; 548/318.5; 514/369; 514/376; 514/389; 514/390
(58) Field of Search ..................................... 548/183, 227, 548/226, 318.5; 514/369, 376, 389, 390

(56) References Cited

U.S. PATENT DOCUMENTS

| | | |
|---|---|---|
| 3,609,183 | 9/1971 | DeWald et al. . |
| 3,683,009 | 8/1972 | Middleton . |
| 4,217,366 | 8/1980 | Kikumoto et al. . |
| 4,271,186 | 6/1981 | Forster et al. . |
| 4,284,637 | 8/1981 | Kikumoto et al. . |
| 4,310,534 | 1/1982 | Kikumoto et al. . |
| 4,312,855 | 1/1982 | Grand . |
| 4,326,055 | 4/1982 | Loeliger . |
| 4,716,905 | 1/1988 | Schmued . |
| 4,866,086 | 9/1989 | Boyle et al. . |
| 4,929,635 | 5/1990 | Coquelet et al. . |
| 4,940,707 | 7/1990 | Klaus et al. . |
| 5,087,637 | 2/1992 | Janssen et al. . |
| 5,162,337 | 11/1992 | Elbrecht . |
| 5,171,753 | 12/1992 | Munson, Jr. et al. . |
| 5,189,056 | 2/1993 | Orlando et al. . |
| 5,246,936 | 9/1993 | Treacy et al. . |
| 5,250,562 | 10/1993 | Klaus et al. . |
| 5,314,693 | 5/1994 | Suga ................................... 424/196.1 |
| 5,378,705 | 1/1995 | Klaus et al. . |
| 5,409,953 | 4/1995 | Pettit et al. . |
| 5,430,062 | 7/1995 | Cushman et al. . |
| 5,494,932 | 2/1996 | Cardin et al. . |
| 5,521,160 | 5/1996 | Chucholowski et al. . |
| 5,525,632 | 6/1996 | Obsumi et al. . |
| 5,532,129 | 7/1996 | Heller . |
| 5,559,151 | 9/1996 | Adorante et al. . |
| 5,565,191 | 10/1996 | Raspanti . |
| 5,565,322 | 10/1996 | Heller . |
| 5,569,786 | 10/1996 | Pettit et al. . |
| 5,583,128 | 12/1996 | Bhatnagar . |
| 5,589,506 | 12/1996 | Hashimoto et al. . |
| 5,672,625 | 9/1997 | Cardin et al. . |
| 5,674,906 | 10/1997 | Hatanaka et al. . |
| 5,705,530 | 1/1998 | Adorante et al. . |
| 5,716,928 | 2/1998 | Benet et al. . |
| 5,731,353 | 3/1998 | Ohsumi et al. . |
| 5,733,909 | 3/1998 | Black et al. . |
| 5,767,268 | 6/1998 | Chucholowski et al. . |
| 5,770,620 | 6/1998 | Mjalli et al. .................... 514/415 |
| 5,827,898 | 10/1998 | Khandwala et al. ............. 514/734 |

OTHER PUBLICATIONS

Chem Abstract Online Printout 116:255519, RN=141200–90–0, Hulin et al.*
PCT Search Report, Mailed 10 Sep. 1999, PCT/US99/11001, filed 18 May 1999.
Green, Richard H., "Syntheses of Differanisole A", Tertrahedron Letters, vol.38, No. 26, pp. 4697–4700, 1997, Elsevier Science Ltd.
Reddy, et al., "From Styrenes to Enanitopure a–Arylglycines in Two Steps", J.Am. Chem. Soc. 1998,120,1207–1217.
Pettit et al., "Isolation, Structure, Synthesis, and Antimitotic Properties of Combretastatins B–3 and B–4 From Combretum Caffrum," *Journal of Natural Products,* vol. 51, No. 3, pp. 517–527, 5/1988.

\* cited by examiner

*Primary Examiner*—Samuel Barts
(74) *Attorney, Agent, or Firm*—Pillsbury Winthrop LLP

(57) ABSTRACT

Novel diphenylethylene compounds containing thiazolidinedione or oxazolidinedione moieties are provided which are effective in lowering blood glucose level, serum insulin, triglyceride and free fatty acid levels in animal models of Type II diabetes. In contrast to previously reported thiazolidine compounds, known to lower leptin levels, the present compound increase leptin levels and have no known liver toxicity.

8 Claims, 8 Drawing Sheets

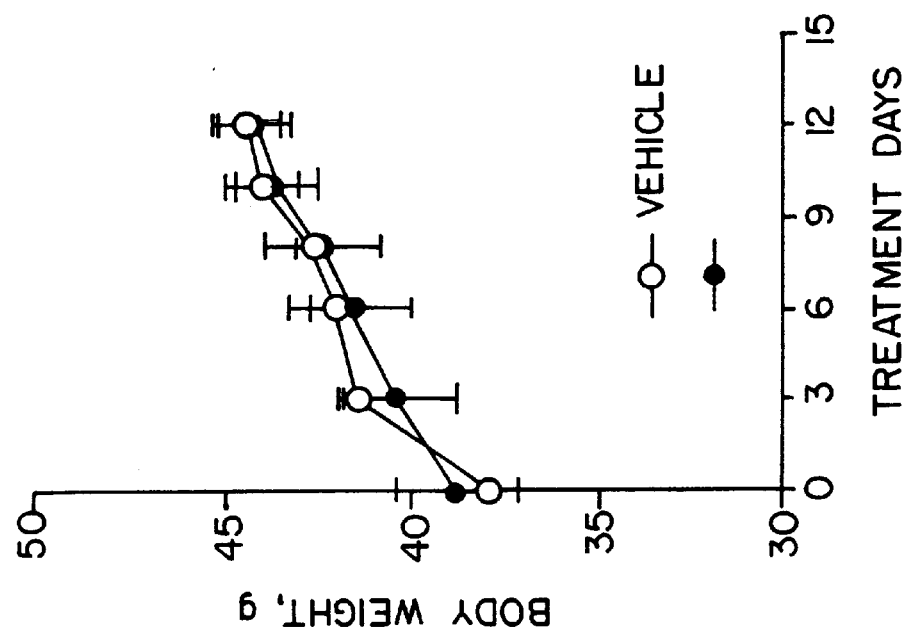
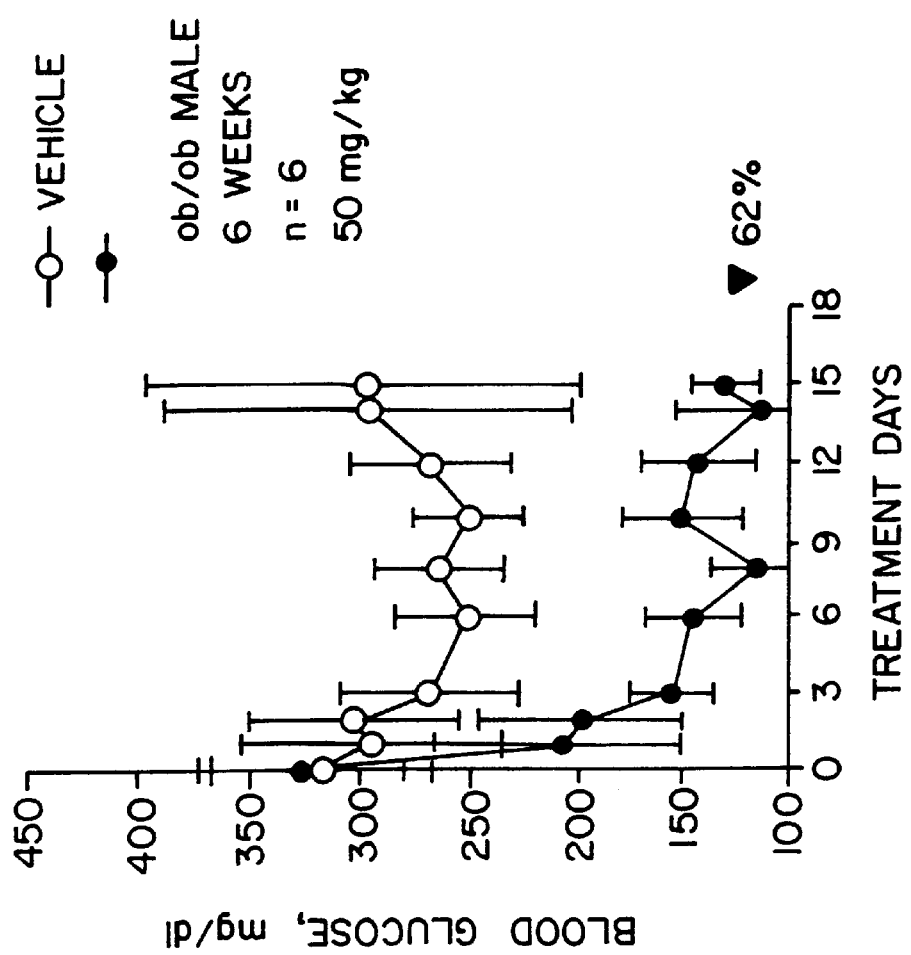
FIG. 2B.
FIG. 2A.

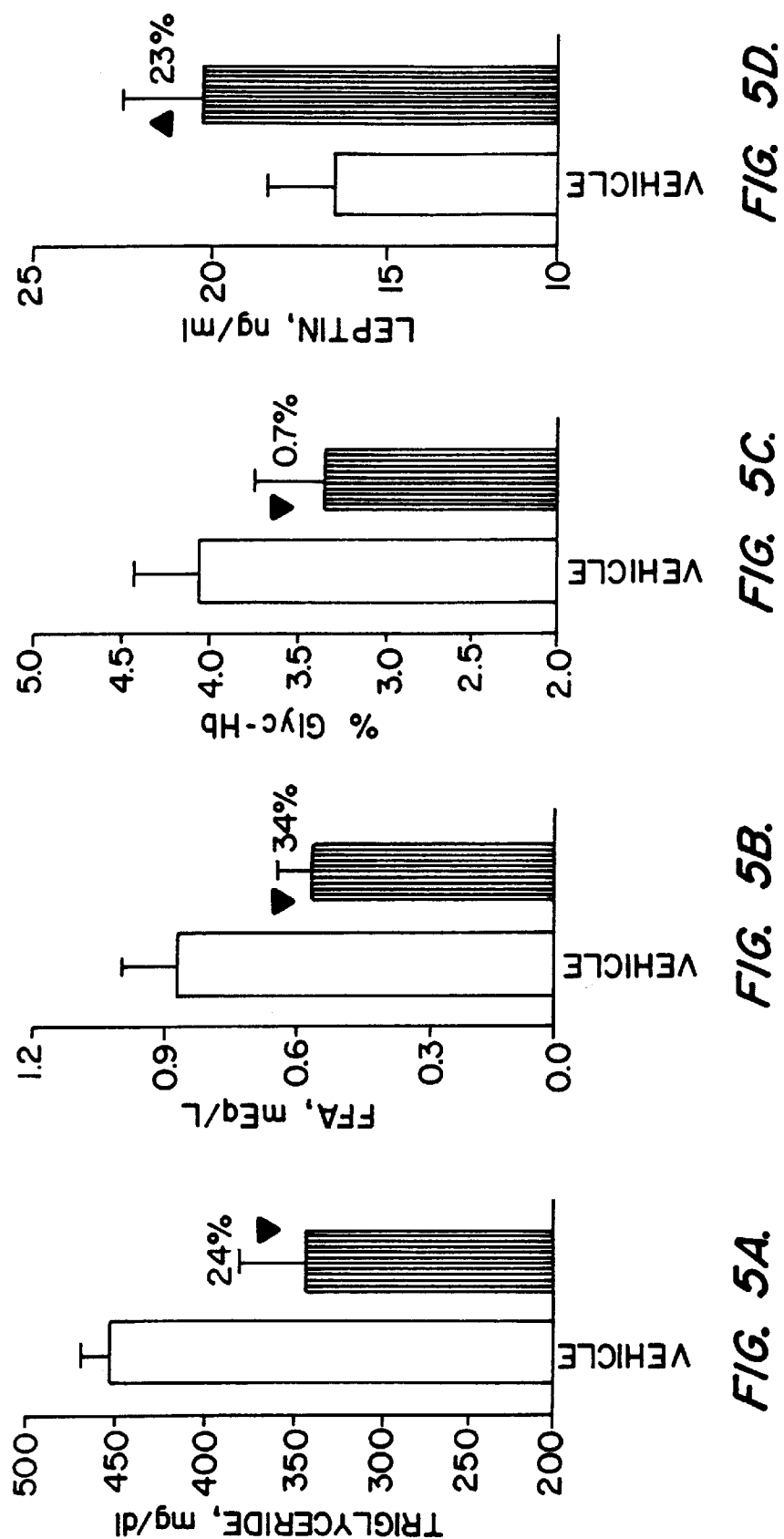

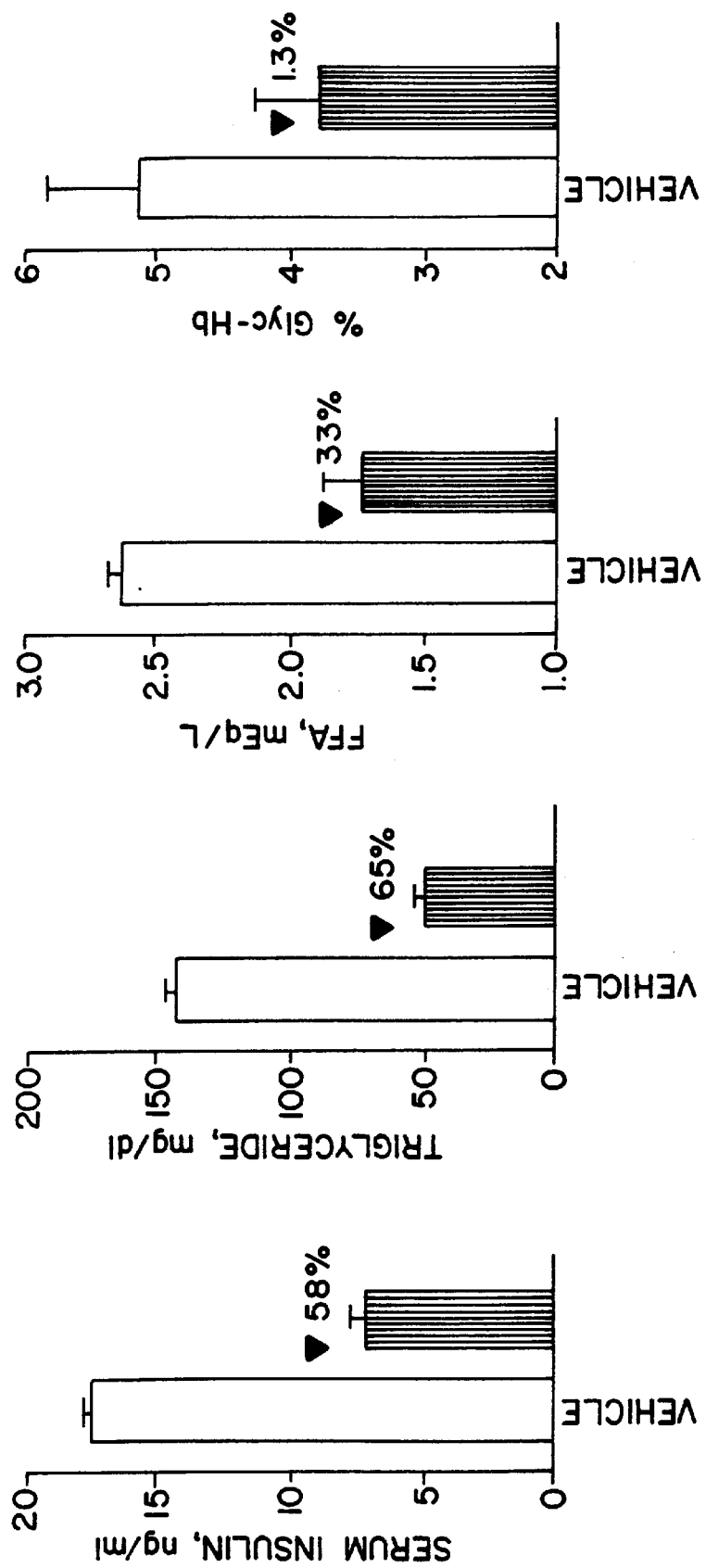

HETEROCYCLIC ANALOGS OF DIPHENYLETHYLENE COMPOUNDS

CROSS REFERENCE TO RELATED APPLICATIONS

This is a continuation-in-part of U.S. application Ser. No. 09/074,925, filed on May 8, 1998, now U.S. Pat. No. 6,245,814.

BACKGROUND OF THE INVENTION

The present application is directed to novel anti-diabetic compounds formed by chemically coupling diphenylethylene compounds with thiazolidine or oxazolidine intermediates. These compounds are effective in lowering blood glucose, serum insulin and triglyceride levels in animal models of type II diabetes. However, surprisingly, these compounds increase the leptin level and have no liver toxicity.

The causes of type I and type II diabetes are yet unknown, although both genetics and environment seem to be the factors. Insulin dependent type I and non-insulin type II are the types which are known. Type I is an autonomic immune disease in which the responsible auto antigen is still unknown. Patients of type I need to take insulin intravenously to survive. However, type II diabetes, the more common form, is a metabolic disorder resulting from the body's inability to make a sufficient amount of insulin or to properly use the insulin that is produced. Insulin secretion and insulin resistance are considered the major defects, however, the precise genetic factors involved in the mechanism remain unknown.

Patients with diabetes usually have one or more of the following defects:

Less production of insulin by the pancreas;

Over secretion of glucose by the liver;

Independent of the glucose uptake by the skeletal muscles;

Defects in glucose transporters, desensitization of insulin receptors; and

Defects in the metabolic breakdown of polysaccharides.

Other than the intravenous application of insulin, there are about 4 classes of oral hypoglycemic agents used.

| Class | Approved Drugs | Mechanisms of Action | Limitations |
|---|---|---|---|
| sulfonylurea | 4 (1st generation) and 2 (2nd generation) | acts on pancreas to release more insulin | dev. of resistance |
| biguanides | metformin | reduces glucose secretion by liver; improves insulin sensitivity | liver problems, lactic acidosis |
| alpha-glucosidase inhibitor | acarbose | interferes with digestive process; reduces glucose absorption | only useful at post-pradiandio level |
| thiazolidine-dione | troglitazone | reduces insulin resistancy | "add-on" with insulin; not useful for people with heart and liver disease |

As is apparent from the above table, each of the current agents available for use in treatment of diabetes has certain disadvantages. Accordingly, there is a continuing interest in the identification and development of new agents, particularly, water soluble agents which can be orally administered, for the use of treatment of diabetes.

SUMMARY OF THE INVENTION

Anti-diabetic compounds of the following formula I are provided:

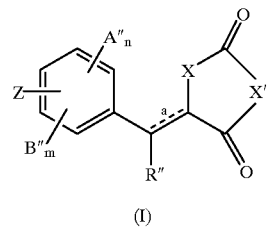

(I)

wherein Z is

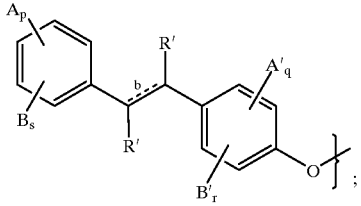

H; A''; ─B''; or

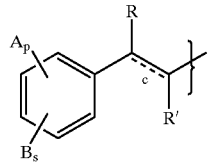

n, m, q and r are independently integers from zero to 4; p and s are independently integers from zero to 5; a, b and c are double bonds which may be present or absent;

R, R' and R'' are independently H, $C_1$–$C_{20}$ linear or branched alkyl, $C_2$–$C_{20}$ linear or branched alkenyl, ─$CO_2$H, ─$CO_2$R''', ─$NH_2$, ─NHR''', ─$NR_2$''', ─OH, ─OR''', halo, substituted $C_1$–$C_{20}$ linear or branched alkyl or substituted $C_2$–$C_{20}$ linear or branched alkenyl, wherein R''' is $C_1$–$C_{20}$ linear or branched alkyl or linear or branched alkenyl;

A, A' and A'' are independently H, $C_1$–$C_{20}$ acylamino; $C_1$–$C_{20}$ acyloxy; $C_1$–$C_{20}$ alkanoyl; $C_1$–$C_{20}$ alkoxycarbonyl; $C_1$–$C_{20}$ alkoxy; $C_1$–$C_{20}$ alkylamino; $C_1$–$C_{20}$ alkylcarboxylamino; carboxyl; cyano; halo; hydroxy;

B, B' and B" are independently H;
C$_1$–C$_{20}$ acylamino; C$_1$C$_{20}$ acyloxy; C$_1$–C$_{20}$ alkanoyl; C$_1$–C$_{20}$ alkenoyl; C$_1$–C$_{20}$ alkoxycarbonyl; C$_1$–C$_{20}$ alkoxy; C$_1$–C$_{20}$ alkylamino; C$_1$–C$_{20}$ alkylcarboxylamino; aroyl, aralkanoyl; carboxyl; cyano; halo; hydroxy;

X, X' are independently —NH, —NR''', O or S.

Pharmaceutical compositions containing compounds of the formula I are provided for treatment of diabetes and comprise a therapeutically effective amount of the compound in a physiologically acceptable carrier.

A method of treating diabetes is also provided comprising the step of orally administering to a subject suffering from a diabetic condition a therapeutically effective amount of a compound of formula I.

BRIEF DESCRIPTION OF THE DRAWINGS

FIGS. 2A and 2B show graphs of the blood glucose levels and body weights of ob/ob (genetically obese and spontaneously diabetic) male rats given a compound according to the invention over a period of 15 days.

FIGS. 5A, 5B, 5C and 5D show graphs of the triglyceride levels, free fatty acid levels, glyc-Hb levels and leptin levels in serum of the db/db mice treated with a compound according to the present invention.

FIGS. 6A, 6B, 6C and 6D are graphs showing the serum insulin levels, triglyceride levels, free fatty acid levels and Glyc-Hb levels of serum of ob/ob mice treated with a compound according to the present invention.

DESCRIPTION OF THE PREFERRED EMBODIMENTS

Figure 1B:
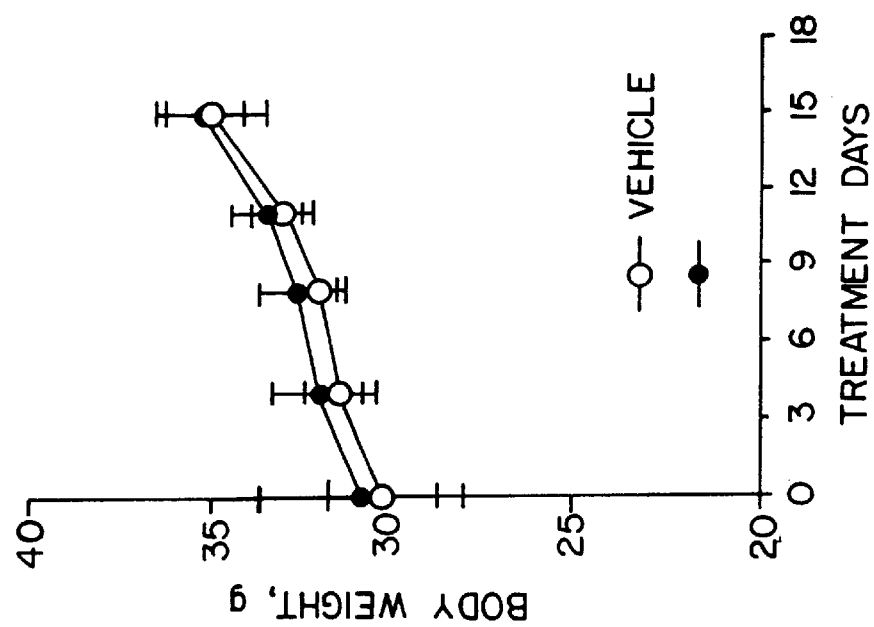
FIGS. 1A and 1B show graphs of the blood glucose levels and body weights, respectively, of db/db (spontaneous diabetic) male rats given a compound according to the invention of a period of 15 days.

Diphenylethylene compounds according to the present may be combined with a physiologically acceptable vehicle in a pharmaceutical composition, such as, lyophilized powder in the form of tablet or capsule with various fillers and binders. The effective dosage of a compound in the composition will be selected by those of ordinary skill in the art and may be empirically determined. The compounds of the present invention are useful for the treatment of diabetes, characterized by the presence of elevated blood glucose levels, that is, hyperglycemic disorders such as diabetes melitis, including both type I and II diabetes. As well as other hyperglycemic related disorders such as obesity, increased chloresterol, kidney related disorders and the like.

By "treatment", it is meant that the compound is administered at least to reduce the blood glucose level in the patient suffering from the hyperglycemic disorder. The compound is administered in the amount sufficient to reduce the blood glucose level, free fatty acid level, cholesterol level, and the like to an acceptable range, where an acceptable range means + or –10%, and usually + or –5% of the normal average blood glucose level of the subject. A variety of subjects may be treated with the compound to reduce blood glucose levels such as livestock, wild or rare animals, pets, as well as humans. The compounds may be administered to the subject suffering from the hyperglycemic disorder using a convenient administration technique, including intravenous, intradermal, intramuscular subcutaneous, oral and the like. However, oral dosage is preferred. The dosage delivered to the host will necessarily depend upon the route by which the compound is delivered, but generally ranges from about 5–500 mg/kg human body weight or typically from about 50 to 200 mg/kg human body weight.

Of particular interest are methods of treating human hyperglycemic disorders such as diabetes, including type I and II, where the compound is administered to the human suffering from the hyperglycemic disorder to at least reduce the blood glucose level of the subject to amount the normal blood glucose range for a human.

Representative compounds according to the present invention may be synthesized by the methods disclosed below in Schemes IA, IB, II and III.

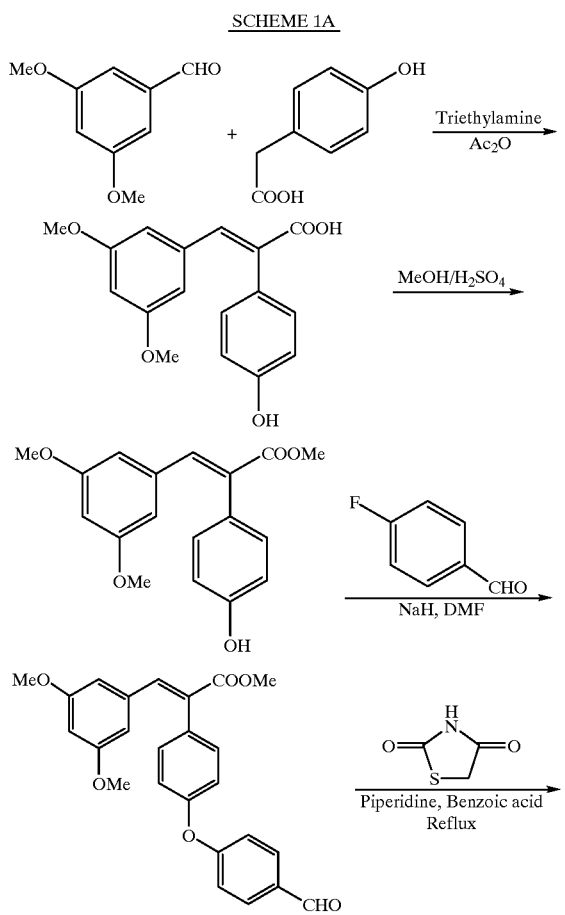

SCHEME 1A

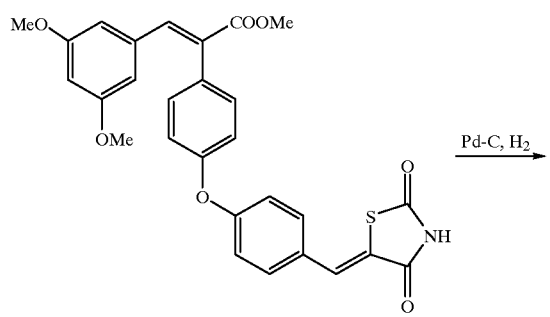
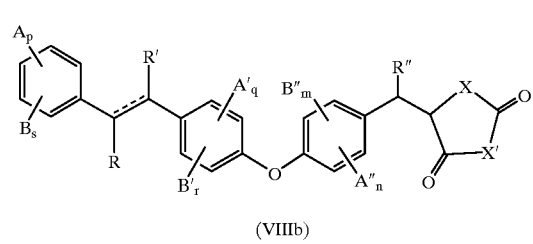
SCHEME IB
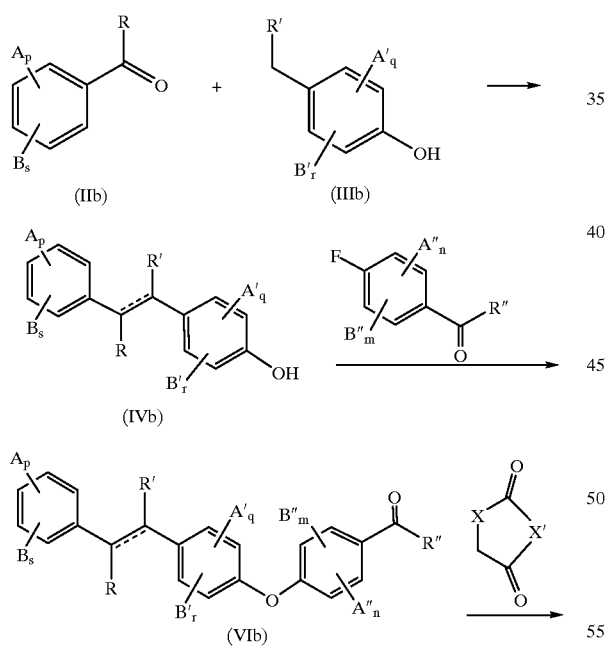
SCHEME II
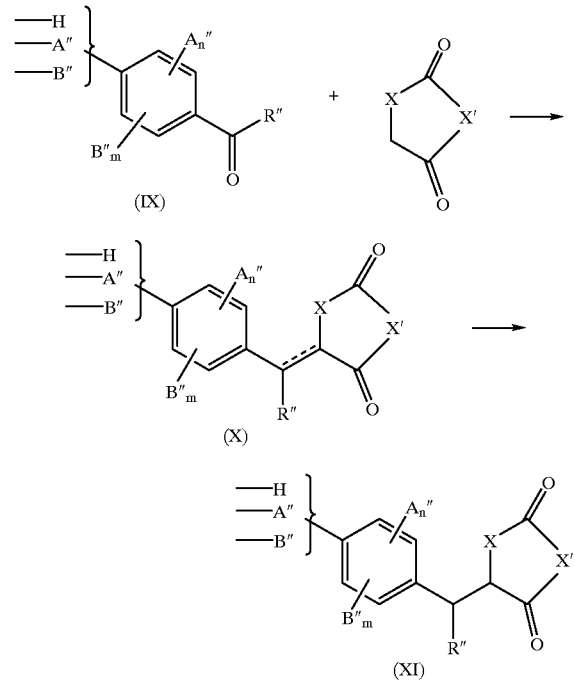
SCHEME III
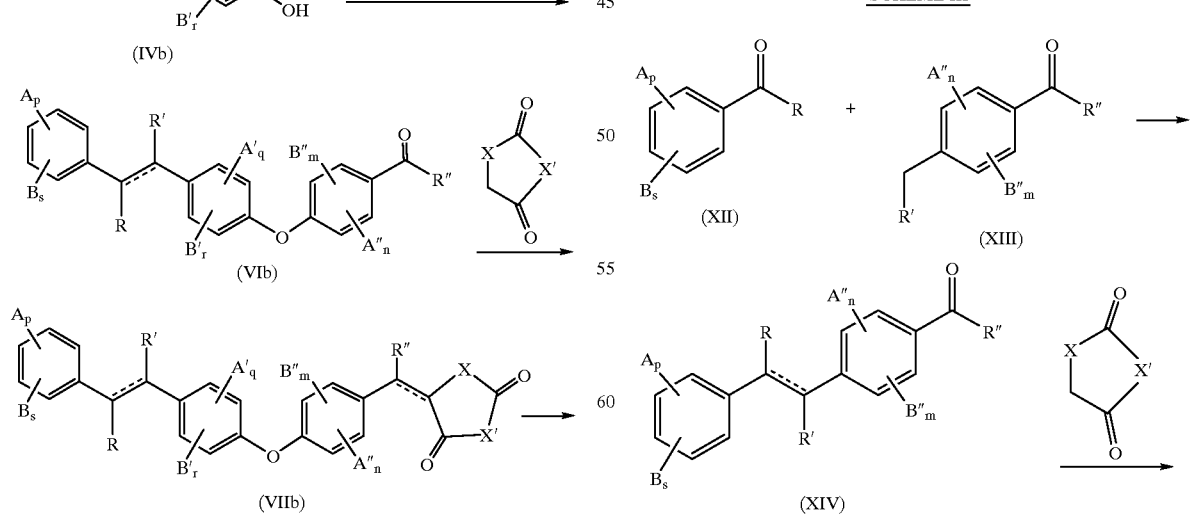

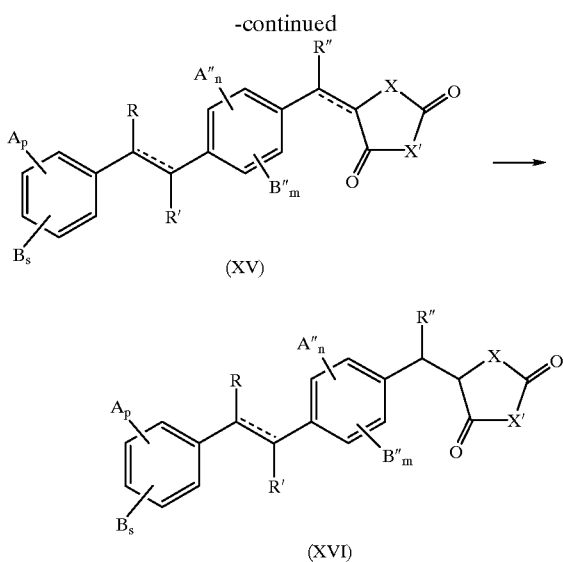

(XV)

(XVI)

Referring to Scheme IA, the aldehyde (II) and acid (III) may be condensed in acetic anhydride and triethylamine to form the unsaturated acid (IV). After esterification of the acid, the phenolic hydroxy group is formed into an ether (VI) with p-fluorobenzaldehyde. The aldehyde (VI) is then condensed with the thiazolidinedione and the two non-cyclic double bonds are reduced with hydrogen to form the object compound (VIII).

The steps in Scheme IA are generalized in Scheme IB. The general formulas IIIB, IVB, VIB, VIIB and VIIIB correspond respectively to formulas III, IV, VI, VII and VIII in Scheme IA.

In Scheme II, the general synthesis of compounds where Z=—H, —A" or —OB" is shown. The aldehyde or ketone (IX) is condensed with the heterocyclic dione to form the bicyclic compound (X), which can be optionally hydrogenated to form the product (XI).

In Scheme III, the general synthesis of the tricyclic products (XV) and (XVI) is shown. The aldehyde or ketone (XII) is condensed with (XIII) to form the bicyclic compound (XIV). The compound (XIV) is condensed with the heterocyclic dione to form the tricyclic product (XV), which can be optionally hydrogenated to (XVI).

In formula I, $C_1$–$C_{20}$ linear or branched alkyl means groups such as methyl, ethyl, propyl, isopropyl, n-butyl, isobutyl, t-butyl, sec-butyl, isopentyl, neopentyl, etc. The $C_2$–$C_{20}$ linear or branched alkenyl means unsaturated groups such as ethenyl, propenyl, n-butenyl, isobutenyl, including groups containing multiple sites of unsaturation such as 1,3-butadiene, and the like. The halo groups include fluoro, bromo, iodo. Substituted $C_1$–$C_{20}$ linear or branched alkyl or substituted $C_2$–$C_{20}$ linear or branched alkenyl means that the alkyl or alkenyl groups may be substituted with groups such as halo, hydroxy, carboxyl, cyano, amino, alkoxy, and the like. The $C_1$–$C_{20}$ acylamino or acyloxy group means an oxygen or amino group bonded to an acyl group (RCO) where R can be hydrogen, $C_1$–$C_{20}$ linear or branched alkyl or $C_2$–$C_{20}$ linear or branched alkenyl. Alkenyl groups are —C=C—, where R can be hydrogen, $C_1$–$C_{20}$ linear or branched alkyl or $C_2$–$C_{20}$ linear or branched alkyl. Alkoxycarbonyl means a group ROCO— where R can be hydrogen, $C_1$–$C_{20}$ linear or branched alkyl or $C_2$–$C_{20}$ linear or branched alkenyl. The $C_1$–$C_{20}$ alkyl carboxyl amino group means a group RCON(R)— where R can be independently hydrogen, $C_1$–$C_{20}$ linear or branched alkyl or $C_2$–$C_{20}$ linear or branched alkenyl. Carboxyl is the group $HOC_2$—, and alkanoyl is the group RCO— wherein R is a linear or branched carbon chain. The group aroyl is Ar—CO— wherein Ar is an aromatic group such as phenyl, naphthyl, substituted phenyl, and the like. Aralkanoyl is the group Ar—R—CO— wherein Ar is a aromatic group such as phenyl, naphthyl, substituted phenyl, etc. and R is a linear branched alkyl chain.

Figure 1A:
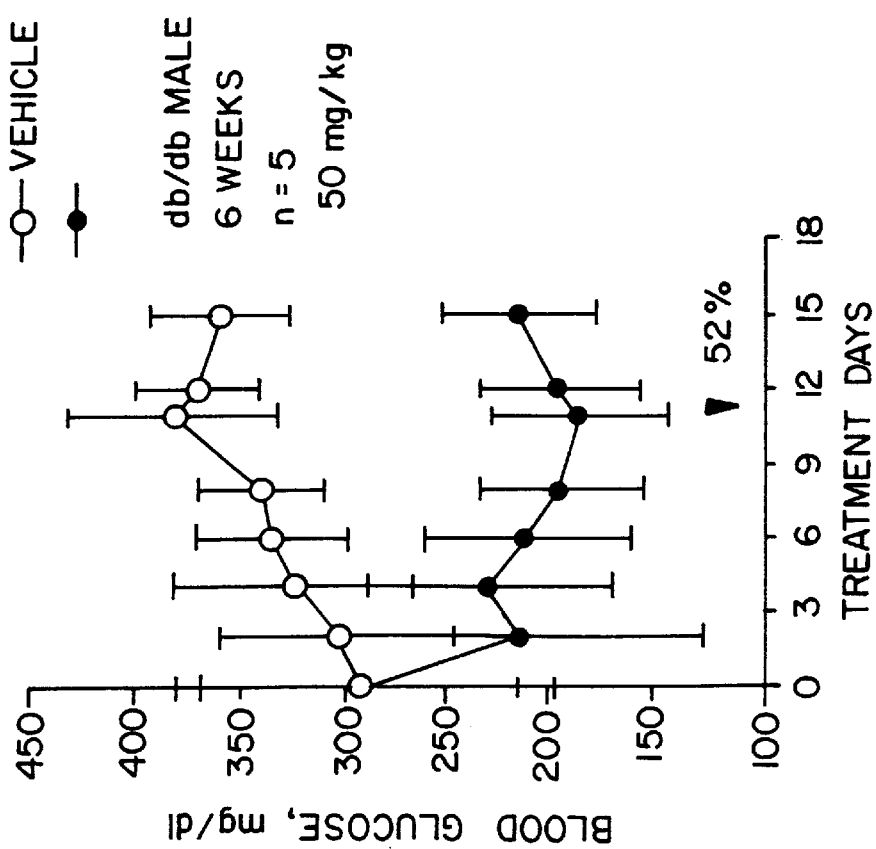

Referring to the figures, a compound according to the present invention, 5-(4-(4-(1-carbomethoxy)-2-(3,5-dimethoxy phenyl)-ethyl)-phenoxy)-benzyl)-2,4-thiazolidinedione (VIII), was administered in a single oral dose (50 mg/kg body weight) for 15 days to db/db male mice as shown in FIG. 1A. A substantial reduction in blood glucose level was observed. There was no increase in body weight in the treatment group as compared to the control treated with the vehicle without the active ingredient, FIG. 1B.

Figure 3B:
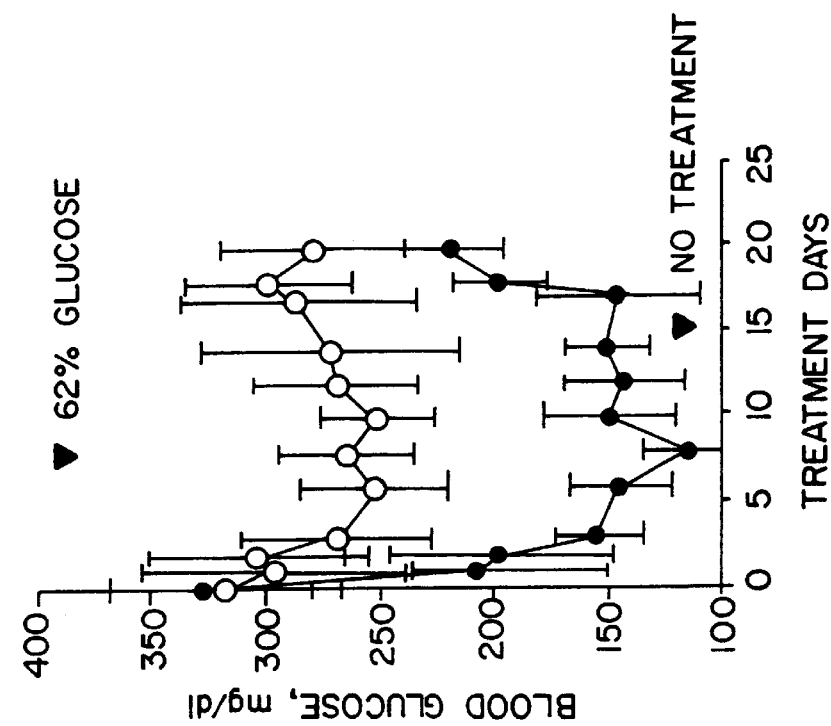
FIGS. 3A and 3B with graphs of blood glucose levels of db/db mice and ob/ob mice, respectively, given a compound according to the invention over a period of 20–25 days.
Figure 3A:
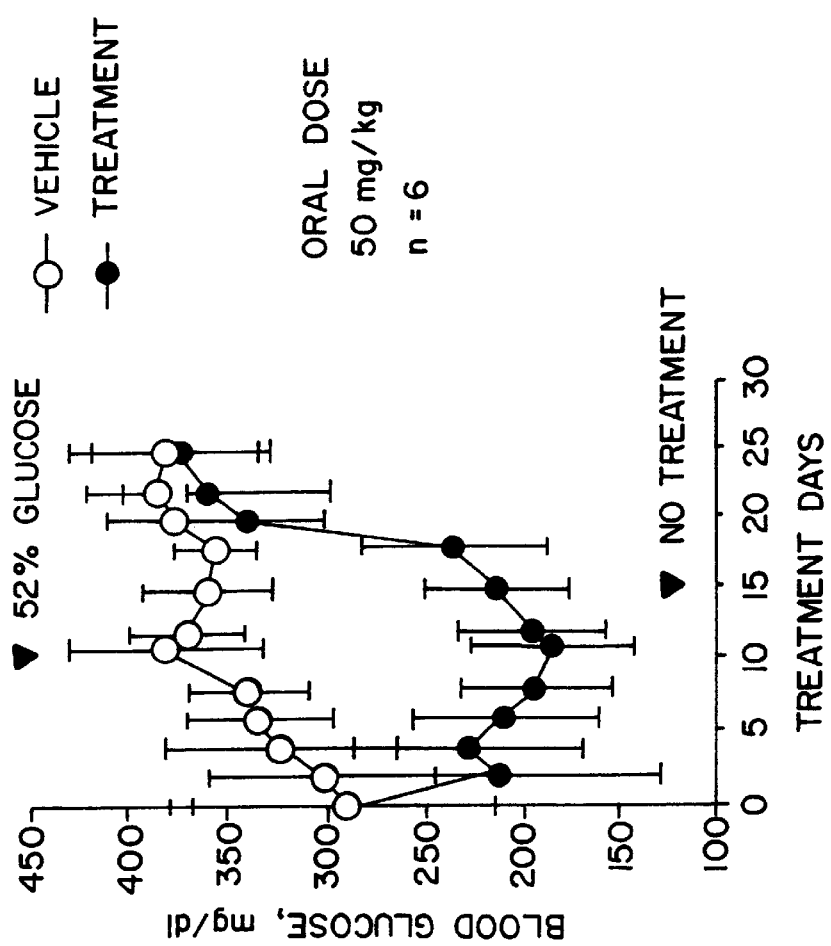
Figure 4:
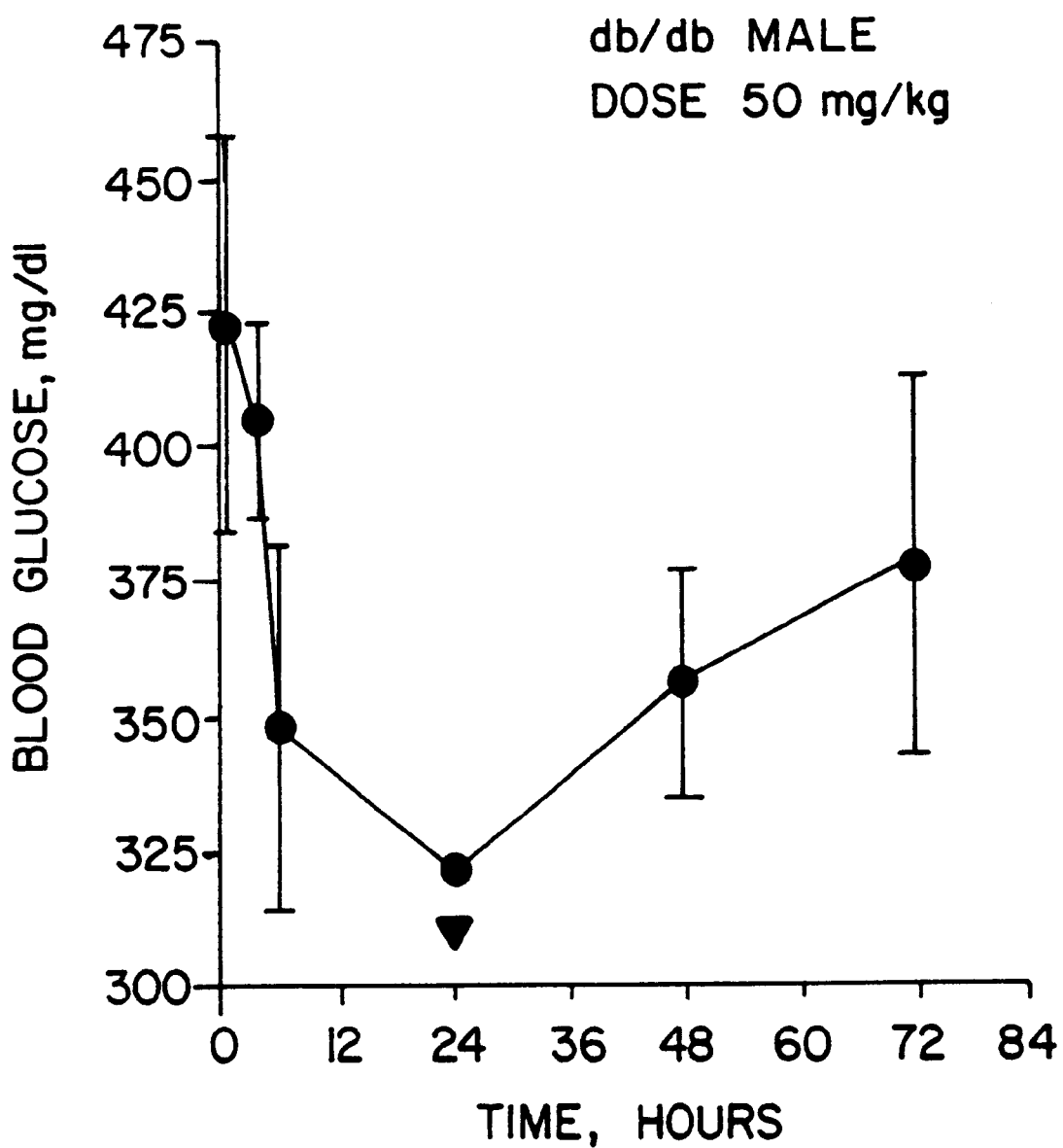
FIG. 4 shows a graph of blood glucose level in db/db male mice over 72 hours following a dosage of the compound.

The compound was orally administered to ob/ob mice with a single oral dose (50 mg/kg body weight). As shown in FIG. 2A, there was a 62% drop in blood glucose level and, similar to db/db mice, there was no significant increase in body weight between the control and the treatment groups as shown in FIG. 2B. This is in contrast to treatment of diabetic animals by thiazolidine type compounds which are known to be associated with increase in body weight. See Okuno et al., *J. Clin. Invest.*, 101, 1354–1361 (1998) and Yoshioka et al., *Metabolism*, 42, 75–80 (1993). By stopping treatment after day 15 in both models, there was shown an increase in glucose level as depicted in FIGS. 3A and 3B. The time course of the drug effect is shown in FIG. 4. Oral administration of a single dose of the compound in db/db mice was effective for 24 hours and beyond.

The triglyceride levels were also measured. Triglycerides, which are esters of fatty acids and glycerol, do not freely circulate in plasma but are bound to proteins and transported as macromolecular complexes called lipoproteins. The triglycerides were measured by the enzymatic method described by McGowen et al., 1983, with a modification to determine the triglyceride levels in db/db and ob/ob mice. There was shown a 24% drop in triglyceride levels in db/db mice (FIG. 5A) after 15 days of treatment with the compound and in ob/ob mice, a 65% decrease in triglyceride as compared to the control (FIG. 6B) after treatment for 10 days.

The free fatty acids (FFA) were enzymatically measured using coenzyme A in the presence of acyl CoA synthase (Wako Chemicals USA). The free fatty acid levels in db/db and ob/ob mice treated with the compound were significantly lower compared to the control animals. A 34% drop in FFA levels in db/db mice (FIG. 5B) were shown after 15 days of treatment with the compound. In ob/ob mice, after 10 days of treatment, a lowering of 33% of FFA was shown compared to the control (FIG. 6C).

The percentage of glycohemoglobin (GHb) in blood reflects the average blood glucose concentration. It is a measure of overall diabetic control and can be use to monitor the average blood glucose levels. The glycosolation of hemoglobin occurs continuously in the red blood cells. But since the reaction is non-enzymatic and irreversible, the concentration of glycohemoglobin in a cell reflects the average blood glucose levels seen by the cell during its life. An assay was conducted using affinity chromatography with boronate as described by Abraham et al., *J. Lab. Clin. Med.*, 102, 187 (1983). There is a 0.7% drop in the GHb level in db/db mice (FIG. 5C) after 15 days of treatment with the compound and in ob/ob mice after 14 days of treatment, there is 1.3% decrease (FIG. 6D) in the GHb level compared to the control.

The blood insulin level was measured by ELISA following a standard protocol. A 58% drop of serum insulin in ob/ob mice (FIG. 6A) was shown after 10 days of treatment with the compound, thus, demonstrating its ability to act as an insulin sensitizer.

Obesity is considered as significant risk factor for various adult diseases such as diabetes and cardiac disease. Leptin, an obese gene product, has been identified from the investigation of ob/ob mice, where the leptin is lacking because of a mutation in that gene (Zhiang et al., Nature, 372, 425 (1994). Leptin is a protein of about 16 kDa, which is expressed in adipose tissue, and which promotes weight loss by suppressing appetite and stimulating metabolism. It is currently believed that leptin plays a key role in the obesity syndrome. In the db/db mice according to the experiment, the leptin level was measured by an ELISA, following a standard protocol. After 15 days of treatment with the compound, there is a 23% increase (FIG. 5D) in the serum leptin level compared to the control group.

Figure 7A:
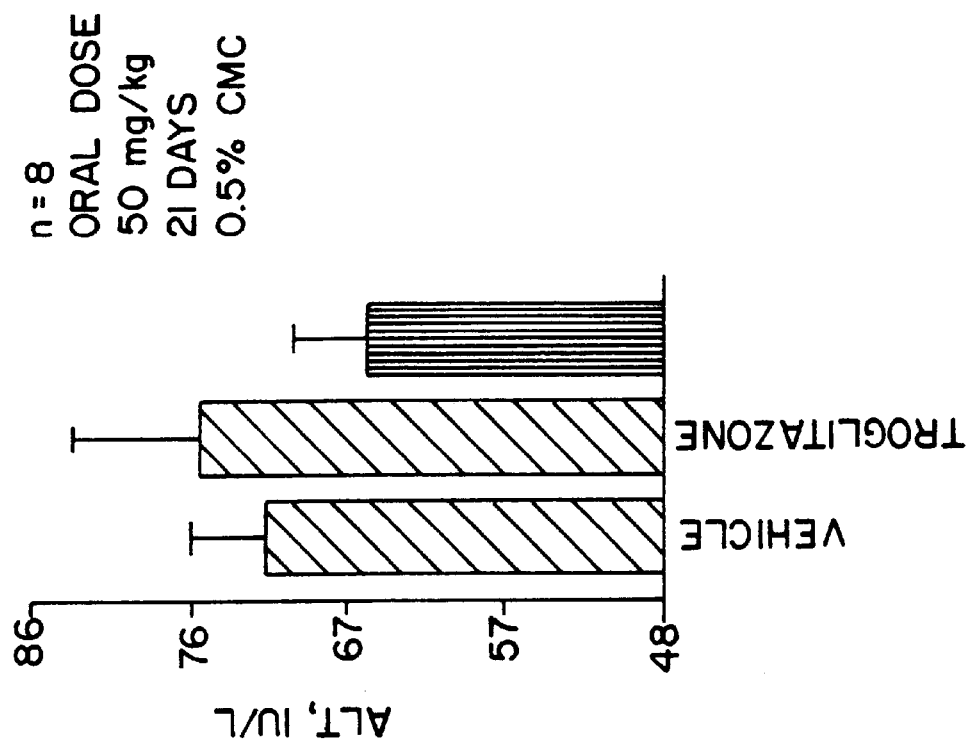
FIGS. 7A and 7B show the assays of liver enzymes in mice 21 days after treatment with a compound according to the invention.
Figure 7B:
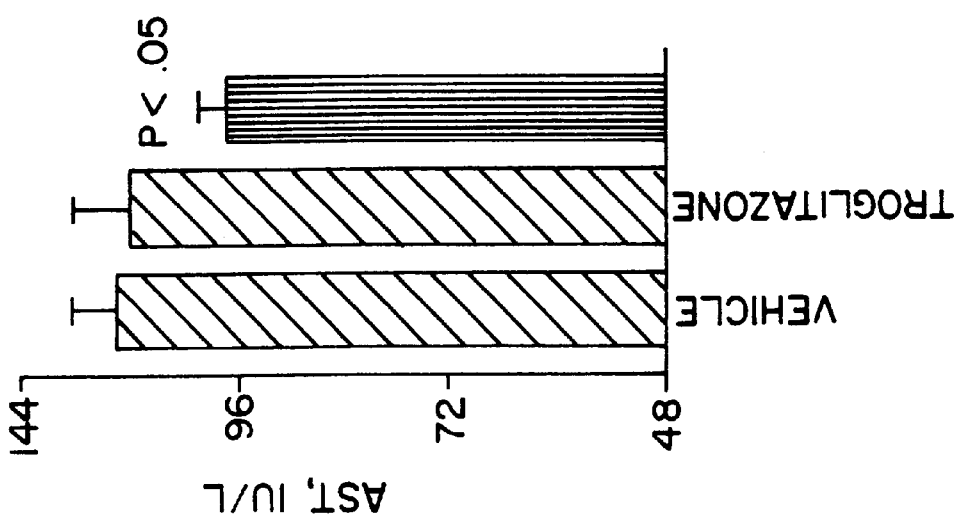

The liver enzymes glutamic oxalacetic transaminase/aspartate aminotransferase (AST/GOT) and glutamic pyruvic transaminase/alanine aminotransferase (ALT/GPT) were assayed in the sera of ob/ob mice after 21 days of treatment (orally, 50 mg/kg) of the test compound. The test was also conducted using troglitazone. These enzyme levels are found to elevate in several kinds of hepatic disorders or liver necrosis. In FIG. 7A, the AST level in the mice was not elevated compared to untreated mice or to mice treated with troglitazone. Similarly, FIG. 7B shows that the ALT level did not elevate compared to untreated mice or mice treated with troglitazone.

Figure 8B:
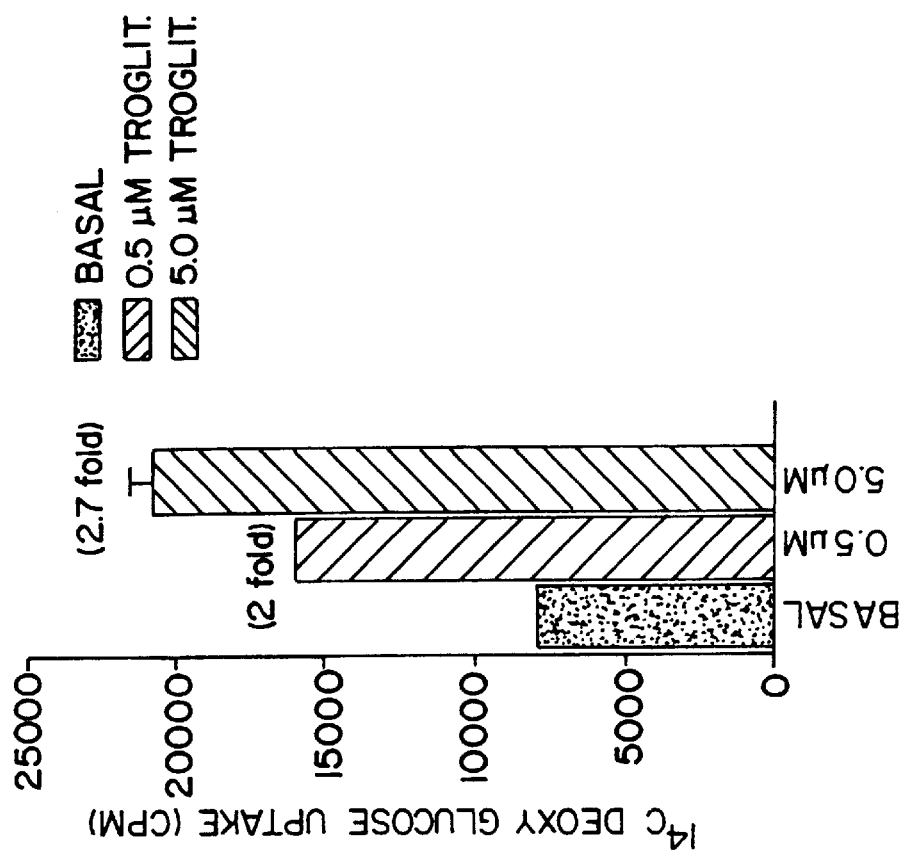
FIGS. 8A and 8B show the glucose uptake assays in 3T3-L1 cells for a compound of the invention and troglitazone.
Figure 8A:
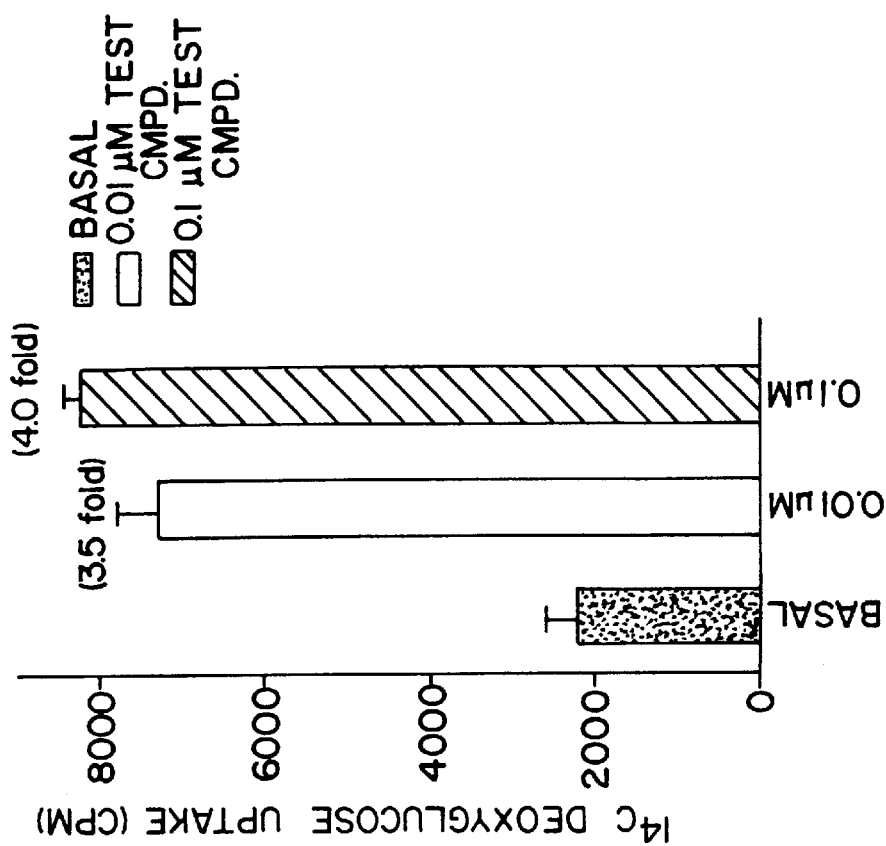

Referring to FIGS. 8A and 8B glucose uptake in 3T3-L1 differentiated adipocytes was measured after treatment with trogliazone or the test compound. The assay was conducted according to the method of Tafuri, Endocrinology, 137, 4706–4712 (1996). The serum-starved cells were treated with the test compound (or troglitazone) for 48 hours at different concentrations, then washed and incubated in glucose-free media for 30 minutes at 37° C. Then $^{14}$C-deoxyglucose was added and uptake was monitored for 30 minutes under incubation. After washing, the cells were lyzed (0.1% SDS) and counted. As shown in FIG. 8A, there is a 3.5 to 4-fold increase in glucose uptake at the indicated concentrations of the test compound with respect to basal levels. There was only a 2 to 2.7-fold increase in uptake using troglitazone at 50× the concentration of the test compound as shown in FIG. 8B.

Accordingly, it is seen that the above tests show that the compounds according to the present invention not only lower blood glucose level, triglyceride level, free fatty acid level, glycohemoglobin and serum insulin, but also raise the leptin level while showing no significant increase in body weight or liver toxicity.

What is claimed is:

1. A compound of formula I:

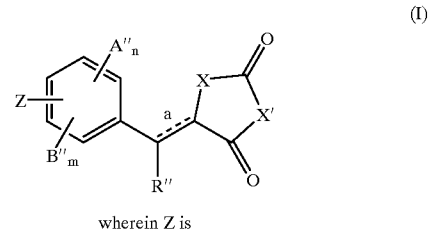

(I)

wherein Z is

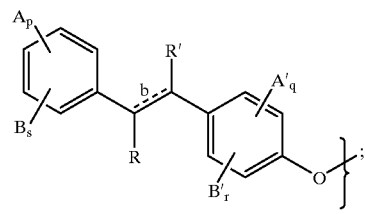

n, m, q and r are independently integers from zero to 4; p and s are independently integers from zero to 5; a and b are bonds which may be independently single or double bonds;

R, R' and R" are independently H, $C_1$–$C_{20}$ linear or branched alkyl, $C_2$–$C_{20}$ linear or branched alkenyl, —$CO_2H$, —$CO_2R'''$, —$NH_2$, —$NHR'''$, —$NR_2'''$, —OH, —OR''', halo, substituted $C_1$–$C_{20}$ linear or branched alkyl or substituted $C_2$–$C_{20}$ linear or branched alkenyl, wherein R''' is $C_1$–$C_{20}$ linear or branched alkyl or linear or branched alkenyl, A, A' and A" are independently H, $C_1$–$C_{20}$ acylamino; $C_1$–$C_{20}$ acyloxy; $C_1$–$C_{20}$ alkanoyl; $C_1$–$C_{20}$ alkoxycarbonyl; $C_1$–$C_{20}$ alkoxy; $C_1$–$C_{20}$ alkylamino; $C_1$–$C_{20}$ alkylcarboxylamino; carboxyl, cyano; halo; hydroxy;

B, B' and B" are independently H; $C_1$–$C_{20}$ acylamino; $C_1$–$C_{20}$ acyloxy; $C_1$–$C_{20}$ alkanoyl; $C_1$–$C_{20}$ alkenoyl; $C_1$–$C_{20}$ alkoxycarbonyl; $C_1$–$C_{20}$ alkoxy; $C_1$–$C_{20}$ alkylamino; $C_1$–$C_{20}$ alkylcarboxylamino; aroyl, aralkanoyl; carboxyl, cyano; halo; hydroxy; and X, X' are independently —NH, —NR''', O or S.

2. A compound according to claim 1, wherein X is sulfur, X' is —NH—; A"$_n$, B", B', A$_p$, A$_q$, R and R" are all hydrogen.

3. A compound according to claim 2, wherein B is methoxy, s=2 and R' is carbomethoxy.

4. A compound according to claim 3, wherein said compound is 5-(4-(4-(1-carbomethoxy-2-(3,5-dimethoxy phenyl)ethenyl)-phenoxy)-benzyl)-2,4-thiazolidinedione.

5. A pharmaceutical composition for treatment of diabetes comprising a therapeutically effective amount of a compound of the formula I:

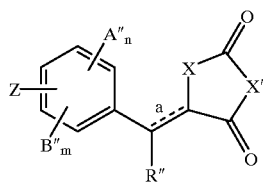

(I)

wherein Z is

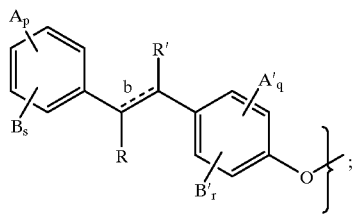

n, m, q and r are independently integers from zero to 4; p and s are independently integers from zero to 5; a and b are bonds which may be independently single or double bonds;

R, R' and R" are independently H, $C_1$–$C_{20}$ linear or branched alkyl, $C_2$–$C_{20}$ linear or branched alkenyl, —$CO_2H$, —$CO_2R'''$, —$NH_2$, —$NHR'''$, —$NR_2'''$, —OH, —OR''', halo, substituted $C_1$–$C_{20}$ linear or branched alkyl or substituted $C_2$–$C_{20}$ linear or branched alkenyl, wherein R''' is $C_1$–$C_{20}$ linear or branched alkyl or linear or branched alkenyl, A, A' and A" are independently H, $C_1$–$C_{20}$ acylamino; $C_1$–$C_{20}$ acyloxy; $C_1$–$C_{20}$ alkanoyl; $C_1$–$C_{20}$ alkoxycarbonyl; $C_1$–$C_{20}$ alkoxy; $C_1$–$C_{20}$ alkylamino; $C_1$–$C_{20}$ alkylcarboxylamino; carboxyl, cyano; halo; hydroxy;

B, B' and B" are independently H; $C_1$–$C_{20}$ acylamino; $C_1$–$C_{20}$ acyloxy; $C_1$–$C_{20}$ alkanoyl; $C_1$–$C_{20}$ alkenoyl; $C_1$–$C_{20}$ alkoxycarbonyl; $C_1$–$C_{20}$ alkoxy; $C_1$–$C_{20}$ alkylamino; $C_1$–$C_{20}$ alkylcarboxylamino; aroyl, aralkanoyl; carboxyl, cyano; halo; hydroxy; and X, X' are independently —NH, —NR''', O or S, in a physiologically acceptable carrier.

6. A composition according to claim 5, wherein X is sulfur, X' is —NH— and A"$_n$, B", B', A$_p$, A'$_q$, R and R" are all hydrogen.

7. A composition according to claim 6, wherein R' is carbomethoxy; B is methoxy and s=2.

8. A composition according to claim 6, wherein said compound is 5-(4-(4-(-1-carbomethoxy-2-(3,5 dimethoxy phenyl)ethenyl)-phenoxy)-benzyl)-2,4-thiazolidinedione.

* * * * *

UNITED STATES PATENT AND TRADEMARK OFFICE
CERTIFICATE OF CORRECTION

PATENT NO. : 6,331,633 B1  Page 1 of 1
DATED : December 18, 2001
INVENTOR(S) : Neogi et al.

It is certified that error appears in the above-identified patent and that said Letters Patent is hereby corrected as shown below:

Column 8,
Line 2, "ethyl" should be replaced with -- ethenyl --.

Signed and Sealed this

Eighteenth Day of October, 2005

JON W. DUDAS
*Director of the United States Patent and Trademark Office*